United States Patent [19]

Racz et al.

[11] Patent Number: 4,552,135

[45] Date of Patent: Nov. 12, 1985

[54] LUMBAR BELT

[76] Inventors: Gabor B. Racz, 4504 17th St., Lubbock, Tex. 79416; Royce C. Lewis, Jr., 5233 W. 19th St., Lubbock, Tex. 79407

[21] Appl. No.: 586,438

[22] Filed: Mar. 5, 1984

[51] Int. Cl.<sup>4</sup> .................................. A61F 5/02
[52] U.S. Cl. ..................... 128/78; 128/DIG. 20
[58] Field of Search ............... 128/78, 96, DIG. 20; 5/449

[56] References Cited

U.S. PATENT DOCUMENTS

| | | | |
|---|---|---|---|
| 1,634,621 | 7/1927 | Martinez | 2/44 |
| 1,924,640 | 8/1933 | Draves | 128/78 |
| 2,181,689 | 11/1939 | Bell | 128/78 |
| 2,372,034 | 3/1945 | Versoy | 128/96 |
| 2,412,075 | 12/1946 | Boone | 128/78 |
| 2,521,530 | 9/1950 | McGuffage | 128/DIG. 20 |
| 2,997,100 | 8/1961 | Morris | 5/450 |
| 3,052,236 | 9/1962 | Schrieber | 128/78 |
| 3,071,133 | 1/1963 | Eisen | 128/78 |
| 3,087,496 | 3/1963 | Norman | 128/78 |
| 3,421,163 | 1/1969 | Stoughton | 5/449 |
| 3,434,469 | 3/1969 | Swift | 128/78 |
| 3,462,775 | 8/1969 | Markwitz et al. | 5/449 |
| 3,568,670 | 3/1971 | Gaylord, Jr. | 128/78 |
| 3,578,773 | 5/1971 | Schultz | 128/78 |
| 3,598,114 | 8/1971 | Lewis | 128/78 |
| 3,717,143 | 2/1973 | Johnson | 128/78 |
| 3,850,164 | 11/1974 | Hare | 128/75 |
| 3,921,222 | 11/1975 | Hollman | 128/78 |
| 4,080,962 | 3/1978 | Berkeley | 128/78 |
| 4,099,523 | 7/1978 | Lowrey | 128/78 |
| 4,099,524 | 7/1978 | Cueman et al. | 128/78 |
| 4,135,503 | 1/1979 | Romano | 128/78 |
| 4,175,548 | 11/1979 | Henry | 128/78 |
| 4,175,553 | 11/1979 | Rosenberg | 128/78 |
| 4,178,922 | 12/1979 | Curlee | 128/78 |
| 4,245,628 | 1/1981 | Eichler | 128/78 |
| 4,475,543 | 10/1984 | Brooks et al. | 128/78 |

Primary Examiner—Paul J. Hirsch
Attorney, Agent, or Firm—Marcus L. Bates

[57] ABSTRACT

A belt for supporting the back and especially for bracing and supporting the lower spinal column, is often referred to as the "small" of the back. The lower marginal end of the spinal column, located at the small of the back, appears to be the first part of a person's back which tires or becomes uncomfortable when a person is driving a vehicle for an extended length of time. This back fatigue also occurs when a person is improperly standing or improperly lifting and carrying heavy objects from one to another location. The present invention is for a belt which adjustably reinforces the small of the back in a manner to reduce fatigue and discomfort, such as referred to above. The belt has a relatively small front belt which girdles the stomach and a relatively large rear belt which is superimposed over the small of the back. The rear belt has a centrally located pad which includes a chamber. The chamber is filled with open cell sponge-like material. A valve connects the chamber with the atmosphere, and controls the flow of air into and out of the chamber. When one compresses the rear belt between his body and the back of a seat, air is expelled through the valve and from the chamber. When the compression force is removed from the rear belt, the sponge-like material forces the chamber walls apart, causing air to flow through the valve and into the chamber.

9 Claims, 7 Drawing Figures

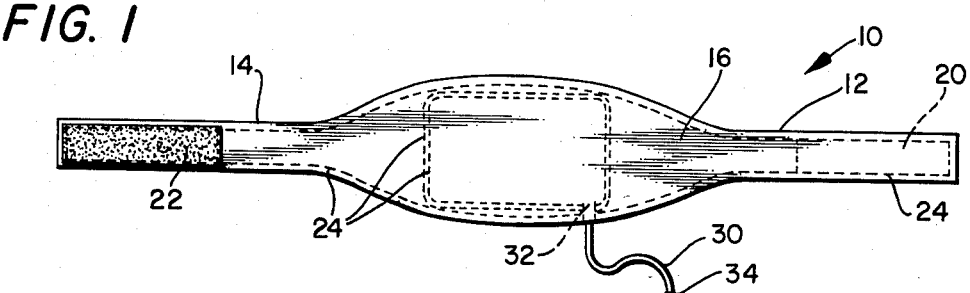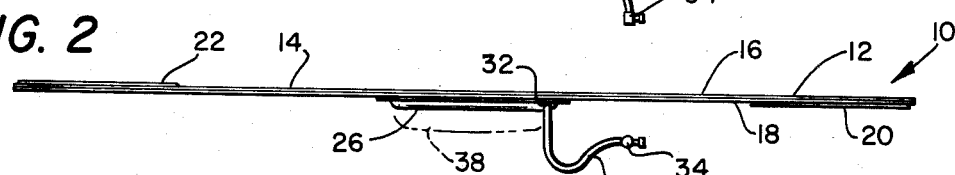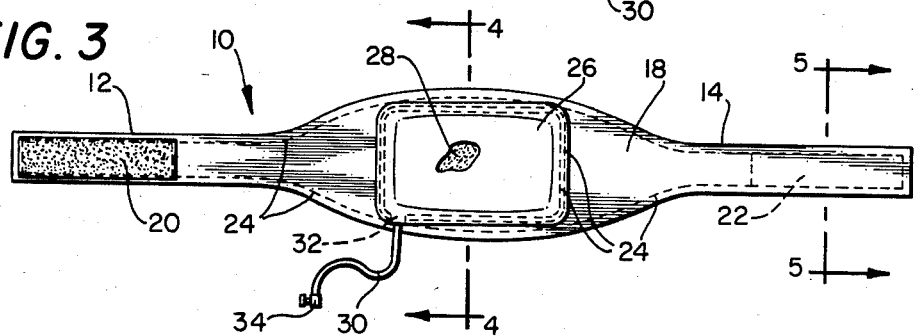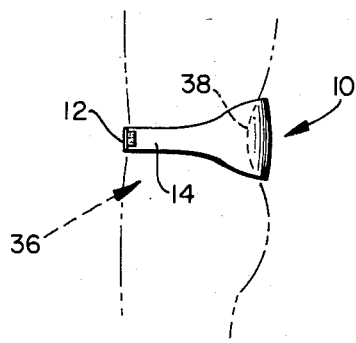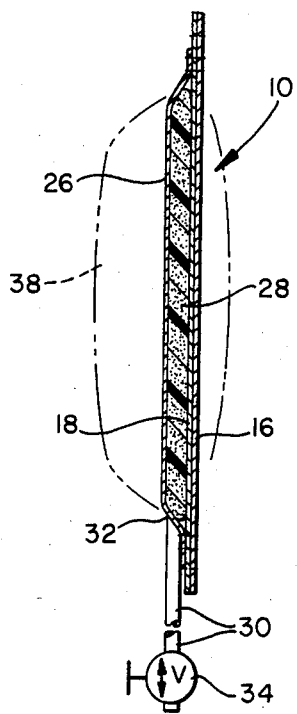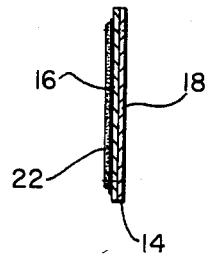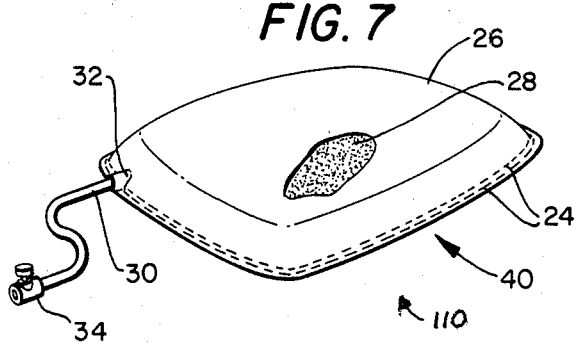

LUMBAR BELT

BACKGROUND OF THE INVENTION

When driving a vehicle for long intervals of time, especially a truck or heavy equipment, discomfort of the back is evident within the first few hours of driving. This is often referred to as "back fatigue" or "back strain". Some truck drivers find it beneficial to insert a small pillow between the seat back and the small of the back. While this alleviates a considerable amount of the back strain, the cushion never seems to be the proper size or the proper thickness, so this use of a cushion is considered a partial solution to the back fatigue problem.

Schrieber, U.S. Pat. No. 3,052,236, discloses a spinal column supporter having a rearwardly directed seal chamber which is filled with cushion material such as gaseous fluid or liquid fluid. Bell, U.S. Pat. No. 3,181,689; Martinez, U.S. Pat. No. 1,634,621; Boone, U.S. Pat. No. 2,412,075; Norman, U.S. Pat. No. 3,087,496; Draves, U.S. Pat. No. 1,924,640; Johnson, U.S. Pat. No. 3,717,143; Rosenburg, U.S. Pat. No. 4,175,553; Swift, U.S. Pat No. 3,434,469; Berkerly, U.S. Pat. No. 4,080,962; and Gaylord, Jr., U.S. Pat. No. 3,568,670 suggest various different back supports which circumferentially enclose the body and supports the back. However, none of these prior art references provide a back support means by which the supported area at the small of the back can be changed in a manner to effect varying degrees of support without having to change the construction of the pads or the like.

Romano, U.S. Pat. No. 4,135,503, discloses a wide belt having fastening means thereon, with there being a support means 12 in the form of a pocket 14 which can adjust predetermined portions of the spine. A bladder 36, FIG. 5, is comprised of two separate members which are movable respective to a base plate 40, and which can be inflated or deflated by means of a pump 75 and 76. Hence, the Romano device must be manually inflated and deflated by the employment of a pump apparatus.

Eichler, U.S. Pat. No. 4,245,628, discloses a support pad 1 having a fastening plate 9 and arch rib plate 11 to which there is mounted an intermediate foam cushion 12.

The present invention differs from the above recited art by the provision of a back support especially suited for bracing and supporting the spinal column at the small of the back by the employment of a novel variable chamber arranged centrally respective to the small of the back, and held into an optimum position by a circumferentially extending belt which snuggly positions a back panel in a manner to locate the cushion within the small of the back. The cushion can be varied in thickness by the wearer without removing the back support, and without the use of a manually operated air pump.

SUMMARY OF THE INVENTION

A back support apparatus has a rear belt which includes an oblated flat center. The rear belt curves into opposed elongated front panels. The front panels extend from the center and terminate in a pair of spaced free ends. The marginal free ends of the front panels have fastener means associated therewith by which the free ends can be attached to one another, thereby attaching the support apparatus to the wearer thereof.

A cushion is attached centrally to the center and is of a size to be received against and provides support at the small of the back. The cushion includes an enclosure means having a marginal peripheral edge attached to the inner surface of the center of the rear belt. Valve means control flow of ambient air into and out of the enclosure. Biasing means is contained within the enclosure for urging the walls of the enclosure apart and thereby effecting a pressure differential between the interior of the enclosure and ambient, so that ambient air controllably flows through the valve and into and out of the enclosure.

In the preferred form of the invention, the biasing means is a sponge-like material which can be compressed to expel air from the enclosure, and which normally expands and urges the enclosure walls apart, to thereby force air to flow from ambient into the enclosure when the valve is in the open position.

The back support apparatus is arranged with the center of the rear belt lying against one's back, and with the cushion positioned centrally respective to the small of the back. The elongated panels are brought about the abdomen and fastened together to thereby enclose the trunk of one's body within the back support apparatus.

The valve is opened whereupon the sponge-like material expands the interior of the enclosure wall apart, causing ambient air to flow into and fill the enclosure. The valve is then closed in order to trap the air within the cushion enclosure. Thereafter, when seated, a person's weight bears against the cushion and compresses the cushion between one's back and the seat back, so that the trapped air can be metered from the enclosure until the optimum support is achieved.

A primary object of the present invention is the provision of a back support having a variable volume cushion associated therewith.

Another object of the present invention is the provision of a back support having a cushion received against the small of the back, with there being means by which the volume of the cushion can be varied by manipulating a valve leading to the interior of the cushion.

Still another object of the present invention is the provision of a back support apparatus having a cushioned center aligned with the small of one's back, and a circumferentially extending panel which girdles a person's trunk and thereby holds the cushion properly aligned at the location which provides maximum comfort for the wearer, and wherein the volume of the cushion can be controlled with a valve device.

These and various other objects and advantages of the invention will become readily apparent to those skilled in the art upon reading the following detailed description and claims and by referring to the accompanying drawings.

The above objects are attained in accordance with the present invention by the provision of a combination of elements which are fabricated in a manner substantially as described in the above abstract and summary.

BRIEF DESCRIPTION OF THE DRAWINGS

FIG. 1 is a side elevational view of a back support made in accordance with the present invention;

FIG. 2 is a top view of the cushion disclosed in FIG. 1;

FIG. 3 is an elevational view of the opposed side of the cushion disclosed in FIG. 1, with some parts being removed therefrom in order to disclose the interior thereof;

FIG. 4 is an enlarged, cross-sectional view taken along line 4—4 of FIG. 3;

FIG. 5 is an enlarged, cross-sectional view taken along line 5—5 of FIG. 3;

FIG. 6 is a reduced, part diagrammatical, part schematical view showing the back support of the present invention in attached relationship respective to a person's trunk; and, FIG. 7 is a perspective view which sets forth a second embodiment of the present invention, with some parts being removed in order to more fully disclose the invention.

DETAILED DESCRIPTION OF THE PREFERRED EMBODIMENTS

In the figures of the drawins, there is disclosed a back support apparatus 10 in the form of a unitary belt which is adapted to girdle the trunk of one's body. The back support apparatus includes opposed, elongated, flexible end panels 12 and 14 which extend from a medial portion of the apparatus. The back support apparatus has an outer face 16 opposed to an inner face 18. Velcro fastener means 20 and 22 are affixed to the marginal free ends of which opposed end panel, thereby adapting the apparatus for use with persons having various different waist sizes.

As diagrammatically indicated by numeral 24 in FIGS. 1 and 3, the belt apparatus is made of multiple fabric-like layers of material which are stitched together to form a relatively flexible belt apparatus which conforms to one's back and abdomen when properly fastened about a person's trunk.

An enclosure 26 has the marginal peripheral edge portion thereof centrally attached to the center panel. The enclosure 26 forms a variable cushion chamber 28 within which there is stored a biasing means by which the interior walls of the enclosure are resiliently urged to expand outwardly, thereby increasing the volume of the chamber 28. Conduit 30 can be of any desired length, and is connected to outlet 32 of the chamber 28 and to a control valve means 34. The control valve means 34 can take on a number of different forms and controls the flow of ambient air into and out of variable chamber 28. Numeral 38 schematically indicates the expanded configuration of the enclosure, as the enclosure is forced from its illustrated deflated configuration at 26 into its inflated configuration, illustrated by the dot-dash lines at numeral 38. Numeral 36 of FIG. 6 indicates the trunk of a person's body.

In FIG. 7, numeral 40 indicates an alternant embodiment of the present invention, which is in the form of a cushion. The cushion has a variable chamber 28, made in accordance with the teachings of FIG. 4. In FIG. 7, the various numerals indicate similar parts previously described in conjunction with the first embodiment of the invention.

The cushion 40 is especially useful for persons who require changes in pillow thickness during the night while sleeping. The cushion 40 can be contoured to conform closely to one's neck, head, and shoulders. The volume of the air chamber 28 of cushion apparatus 40 is controlled in a manner similar to the first embodiment of the invention.

In operation, the valve 34 can be opened either before or after the belt is positioned about one's trunk. Each end of the belt is grasped by one's hands, the center panel is suitably placed against the small of one's back, and each flexible panel is then brought across the stomach in overlapping relationship respective to one another, in the manner of FIG. 6, so that the velcro fasteners can releasably secure the belt in the proper location. The belt preferably is worn slightly lower than an ordinary trousers' belt.

The belt apparatus of this invention is especially beneficial for providing support for persons driving a vehicle. While seated in a vehicle, the valve 34 can be opened, thereby allowing air to be exhausted from the variable chamber 28. Should it be discovered that excess air has been exhausted, the person wearing the belt can lift himself slightly from the back of the seat, thereby relaxing the pressure on the cushion, whereupon the valve 34 can be opened to admit air into the variable chamber. This combination of manipulative actions can be employed to enable the wearer of the belt to achieve the optimum cushioning effect afforded by the belt apparatus.

The embodiment of FIG. 7 is beneficial for use as both a head and a neck pillow. FIG. 7 illustrates one embodiment of a pillow having a variable chamber 28 made in accordance with the teachings of FIG. 4. The pillow 40 of FIG. 7 can be adjustably contoured to fit one's neck by changing the volume of the pillow in the before described manner of operation.

I claim:

1. A back support apparatus for supporting the small of one's back, said apparatus is an elongated, circumferentially extending belt which is adapted to be releasably placed about a person's trunk;

said belt apparatus includes a center panel connected to opposed elongated flexible end panels, the end panels have marginal free ends which terminate in a fastener means by which the opposed free ends can be fastened together and thereby girdle the trunk of a person;

said center panel is adapted to be placed at the small of one's back, and has an inside surface which can be brought to bear against a person's trunk, a variable cushion positioned on said inside surface, said cushion is of a size to be received within the small of one's back;

said cushion is in the form of an enclosure which forms a variable chamber, said variable chamber is connected to the atmosphere by a valve means; biasing means contained within said variable chamber for urging the variable chamber walls to expand outwardly and thereby fill the variable chamber with atmospheric air when said valve means is open.

2. The belt of claim 1 wherein said center panel is relatively wide respective to the width of said end panels, the interior of said cushion is filled with sponge-like material to thereby provide said biasing means; said center panel is relatively wide at a medial length thereof and has upper and lower edges which curve towards one another and join to the relative narrow end panels.

3. The belt of claim 2 wherein the belt apparatus is made of a plurality of layers of flexible material; said marginal free ends of said end panels overlap one another and are fastened together by velcro fastening material.

4. The belt of claim 1 wherein said belt is made of multi-layer fabric material attached to one another in sandwiched relationship to present a flexible belt which can be adjusted to conform to a person's back and stomach.

5. A back support apparatus comprising an oblated center having upper and lower edges which curve towards one another to form relatively narrow opposed elongated panels; said panels terminate in a fastener means at the free ends thereof;

a variable cushion attached centrally to the center, said cushion is of a size to be received against and provide support for the small of one's back;

said cushion is made into the form of an enclosure means; a marginal peripheral edge of said enclosure means is attached to the inside wall surface of said center; a valve means for controlling flow of ambient air into and out of said enclosure means; biasing means contained within said enclosure means for urging the walls of the enclosure means apart and thereby effecting a pressure differential between the interior of the enclosure and ambient so that ambient air flows into and out of said variable cushion when the enclosure walls are forced away and towards one another.

6. The back support apparatus of claim 5 wherein said biasing means is a sponge-like material which can be compressed to expel air from said enclosure, and which expands to cause air to flow into said enclosure, when said valve means is in the open position.

7. A back support device in the form of an elongated belt adapted to be worn circumferentially about a person's trunk;

said belt device includes a relatively wide center panel having opposed ends which curve towards each other and thereby provide opposed flexible, elongated end panels; said end panels have marginal free ends which terminate in a fastener means by which the opposed free ends can be fastened together and thereby girdle the trunk of a person;

said center panel has an inside surface which can be brought to bear against a person's trunk, a variable volume cushion positioned on said inside surface; said cushion is of a size to be received against the small of one's back;

said cushion is in the form of an enclosure having wall surfaces which form a variable chamber; the interior of said chamber is connected to the atmosphere by a valve means; the variable chamber has open cell sponge-like material contained therewithin which urges the variable chamber walls to expand outwardly and thereby fill the enclosure with atmospheric air when the valve is open.

8. The device of claim 7 wherein said cushion is centrally located on the inside surface of said center panel; said center panel is relatively wide at a medial length thereof and has upper and lower edges which curve towards one another and join to the relatively narrow end panels.

9. The device of claim 7 wherein the marginal free ends of said end panels overlap one another and are fastened together by velcro fastening material; said belt is made of multilayers of fabric material which provide a flexible belt for conforming to the trunk of a person.

* * * * *